United States Patent [19]

Kruse et al.

[11] Patent Number: 5,795,750

[45] Date of Patent: Aug. 18, 1998

[54] PROCESS FOR THE CONTINUOUS ENZYMATIC EXTRACTION OF HYDROPHOBIC PRODUCTS AND DEVICE SUITABLE THEREFOR

[75] Inventors: Wolfgang Kruse, Bonn; Udo Kragl; Christian Wandrey, both of Jülich, all of Germany

[73] Assignee: Forschungszentrum Jülich GmbH, Jülich, Germany

[21] Appl. No.: 826,881

[22] Filed: Apr. 7, 1997

Related U.S. Application Data

[63] Continuation-in-part of PCT/DE95/01399, Oct. 7, 1995.

[30] Foreign Application Priority Data

Oct. 11, 1994 [DE] Germany .................. 44 36 149.1

[51] Int. Cl.[6] .................. C12P 13/00; C12P 7/64; C12M 1/12; C12N 11/00

[52] U.S. Cl. .................. 435/128; 435/134; 435/135; 435/136; 435/148; 435/155; 435/174; 435/176; 435/177; 435/180; 435/297.1; 435/297.3; 435/297.4; 435/813; 435/817

[58] Field of Search .................. 435/128, 134, 435/135, 136, 813, 155, 297.3, 297.4, 297.1, 174, 177, 176, 148, 180; 935/817

[56] References Cited

U.S. PATENT DOCUMENTS

| | | | |
|---|---|---|---|
| 3,915,802 | 10/1975 | Kominek | 435/122 |
| 4,795,704 | 1/1989 | Matson | 435/288 |
| 4,800,162 | 1/1989 | Matson | 435/135 |
| 4,939,090 | 7/1990 | Taylor | 435/297.2 |
| 4,956,289 | 9/1990 | Wrasidlo et al. | 435/817 |
| 5,057,421 | 10/1991 | Hofmann et al. | 435/182 |
| 5,077,217 | 12/1991 | Matson et al. | 435/280 |
| 5,080,795 | 1/1992 | Pirkle et al. | 210/643 |
| 5,336,601 | 8/1994 | Iacobucci | 435/297.4 |

*Primary Examiner*—Herbert J. Lilling
*Attorney, Agent, or Firm*—Klaus J. Bach

[57] ABSTRACT

In a process for the continuous enzyme-catalyticzed enzymatic production of hydrophobic products in an aqueous solution of a reaction mixture, the product is extracted from the product containing reaction mixture by way of a product-permeable microporous membrane into an organic solvent and the product-depleted reaction mixture is recycled.

14 Claims, 5 Drawing Sheets

PROCESS FOR THE CONTINUOUS ENZYMATIC EXTRACTION OF HYDROPHOBIC PRODUCTS AND DEVICE SUITABLE THEREFOR

This is a CIP application in International Patent Application PCT/DE95/01399 designating the U.S. and claiming the priority of German application P 44 36 149.1 filed Oct. 7, 1995.

BACKGROUND OF THE INVENTION

The invention relates to a process for the continuous enzymatic extraction of hydrophobic products in an aqueous solution and to a device suitable therefor.

Biotransformations generally and enzymatic processes in particular are becoming more and more important for the synthesis of optically active substances, but also for bulk chemicals, wherein the generally very selective chemical effectiveness of the enzymes which are active in the aqueous environment is utilized.

Difficulties occur when substrates are to be converted and products are generated which are not easily water soluble. To solve this problem, there are various attempts for example the application of the enzymes in a form in which they are immobilized on a solid carrier which is suspended in a homogeneous solution with a water mixable solvent or the inclusion of enzymes in reverse micelles.

The direct presence of organic solvents (water mixable or not water mixable) is tolerated only by a few enzymes which belong to the class of the hydrolases (see for example, WO 89/04784). Such enzymes are utilized generally in a state in which they are two-dimensionally immobilized on a membrane. However, for better utilization of a catalyst with regard to activity- and a product amount-specific consumption as well as easy handling, a catalyst which is homogeneously distributed in a solution is advantageous.

Since, as already mentioned, the presence of relatively large amounts of organic solvent in the reaction space leads to a deactivation or a denaturization of the enzymes, the method according to the invention does not utilize organic solvents in the reaction space. Rather, a substrate concentration corresponding to the maximum solubility thereof is maintained by an indirect continuous feeding of the substrate to be reacted and the hydrophobic product formed (together with substrate rests) is removed from the reaction mixture by way of a selective separation procedure (utilizing a corresponding product permeable membrane of sufficient surface) whereas the water soluble components of the reaction mixture remain unchanged in solution.

SUMMARY OF THE INVENTION

In a process for the continuous enzyme-catalyticzed enzymatic production of hydrophobic products in an aqueous solution of a reaction mixture, the product is extracted from the product-containing reaction mixture by way of a product-permeable microporous membrane into an organic solvent and the product-depleted reaction mixture is recycled.

Perforated membranes are considered to be "microporous" if they have pore sizes down to a few nm particularly $\geq 10$ nm. The upper limit is not critical. A condition however is that the phase limit is stabilized. Then safe operation can be achieved with pore sizes of 10 μm and above. For an intensive exchange, especially with small pore sizes, the membrane thickness should be as small as possible.

Preferably, a micro-porous hydrophobic membrane is utilized, especially a hollow fiber membrane bundle whereby large membrane surfaces and small liquid layer membrane surfaces and small liquid layer thicknesses can be realized which provide for a product separation appropriate for the velocity of the enzymatic product formation.

DE 40 41 896 C1 discloses a method for the enzymatic synthesis of organic compounds, wherein the "organic compound" formed in the reaction space from the enzyme or, respectively, enzymes is separated by a solution diffusion membrane, which includes functional groups with selective interaction with respect to the compound to be separated. For this purpose, for example, sulfanized polymer membranes are utilized and the organic compound is removed from the membrane by pervaporative or pertractive discharge. In the last mentioned case, the "desorption" occurs by a so-called flushing liquid for the cyanhydrine separation, to which methylenchloride, acetic anhydride and alternatively, acetyl chloride are added.

In connection with this variation of a well known selection of components with the aid of membranes, the non-porosity of the membranes is especially pointed out, particularly with reference to the enzyme-membrane reactor with which a reaction mixture of large-molecular enzymes is separated.

In contrast to this procedure, in accordance with the invention, there is a selective product separation of a hydrophobic product from a reaction mixture by a variation of the liquid/liquid extraction wherein an interface formed on micropores—particularly in a counter current flow—is continuously renewed.

In principle, the invention can be implemented by utilizing membrane cartridges which are placed in a production circuit in which the aqueous phase recycles. With such an arrangement, utilizing micro-porous membranes, the enzyme comes into contact, at the membrane-stabilized interface, with the organic solvent which, under certain conditions, may detrimentally affect the enzyme activity. In such cases, preferably a reaction zone containing an immobilized enzyme, suitably in the form of an enzyme membrane reactor is provided.

In accordance with the invention, a product-depleted reaction mixture with enzymes and co-factors dissolved therein can be recycled as a result of the direct introduction of the pure educts and the removal of the hydrophobic products which increases the total turnover number and, consequently, reduces costs.

It is particularly advantageous in accordance with the invention to use hollow fiber bundles of hydrophobic materials such as, if appropriate, fluorized hydrocarbon polymers, especially polypropylene and polyethylene whose relatively high porosity and small wall thickness with relatively small pore sizes make them suitable for a realization of the invention.

The micro-porous membranes used may be hydrophobic or hydrophilic, but they should preferably be hydrophobic.

At the interface formed by the membrane, the organic solvent phase comes into contact with the aqueous phase and (with a hydrophobic membrane) would enter the aqueous phase space for which reason a relatively small positive pressure difference is established between the aqueous and the organic phase.

Below, the invention will be described in greater detail on the basis of the enclosed drawings and an exemplary embodiment:

DESCRIPTION OF A PREFERRED EMBODIMENT

Figure 1:
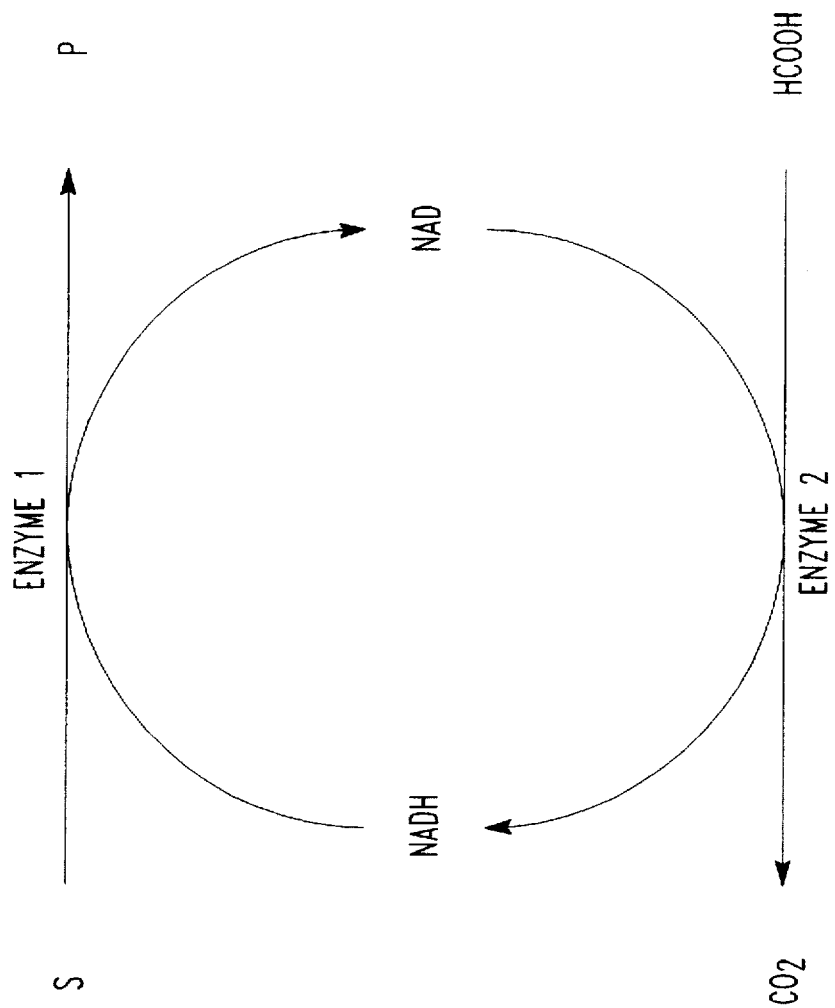
FIG. 1 shows a reaction scheme.

FIG. 1 shows a typical reaction which can be performed in an apparatus according to the invention. A hydrophobic substrate S is converted, in a reaction catalyzed by an enzyme 1, to a hydrophobic product P. Herefor, a cofactor, here NADH, is needed which is reacted to NAD and is regenerated in a second reaction (oxidization of formic acid to $CO_2$) which is catalyzed by an enzyme 2.

Figure 2:
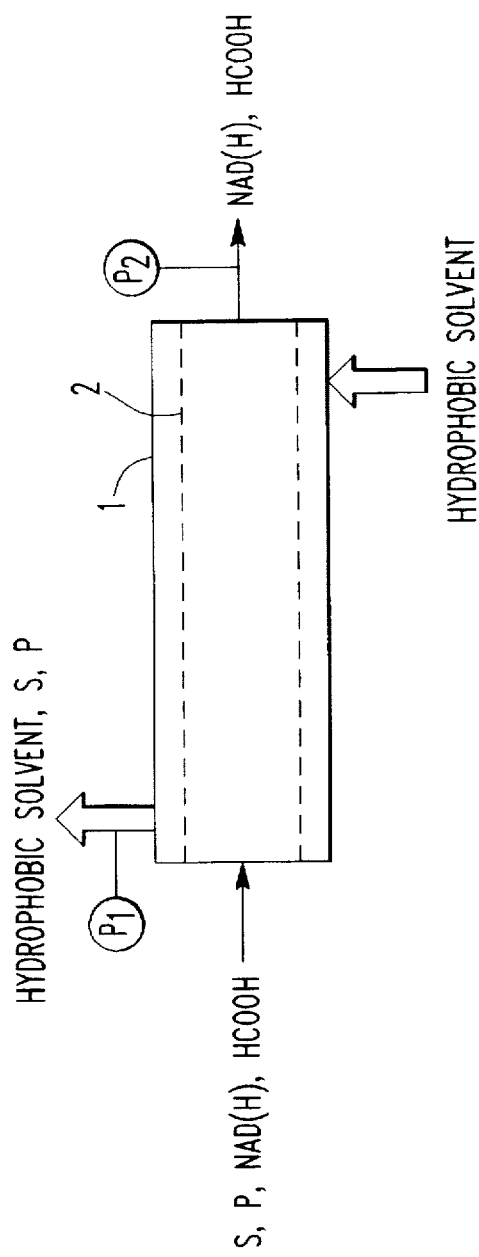
FIG. 2 shows an extraction module.

FIG. 2 shows an extraction module (1) which may be part of an apparatus according to the invention. In this case, substrate S and product P are selectively extracted, by way of a porous membrane (2), from a typical aqueous product solution with buffer, non-reacted substrate S, by enzyme catalyzed reaction obtained product P, cofactor in reduced (NADH) and oxidized form (NAD), and co-substrate (in this case, formic acid (HCOOH)) using a hydrophobic solvent in a counter-current flow relationship. The buffer, the cofactor (NADH) and the cosubstrate remain in the aqueous phase because of their hydrophilic properties.

The membrane (2) serves to stabilize the interface between the hydrophobic and the aqueous phase. The arrangement of the membrane (2) as a hollow fiber bundle provides for large interface surfaces which results in a rapid material transfer.

In order to prevent the hydrophobic solvent from penetrating a hydrophobic porous membrane and entering into the aqueous phase, an excess pressure ($P_2 > P_1$) needs to be provided on the side of the aqueous medium. Similarly, when using a hydrophilic porous membrane, an excess pressure ($P_1 > P_2$) needs to be applied on the side of the hydrophobic solvent in order to prevent transgression of the aqueous reactor solution into the hydrophobic phase.

Figure 3:
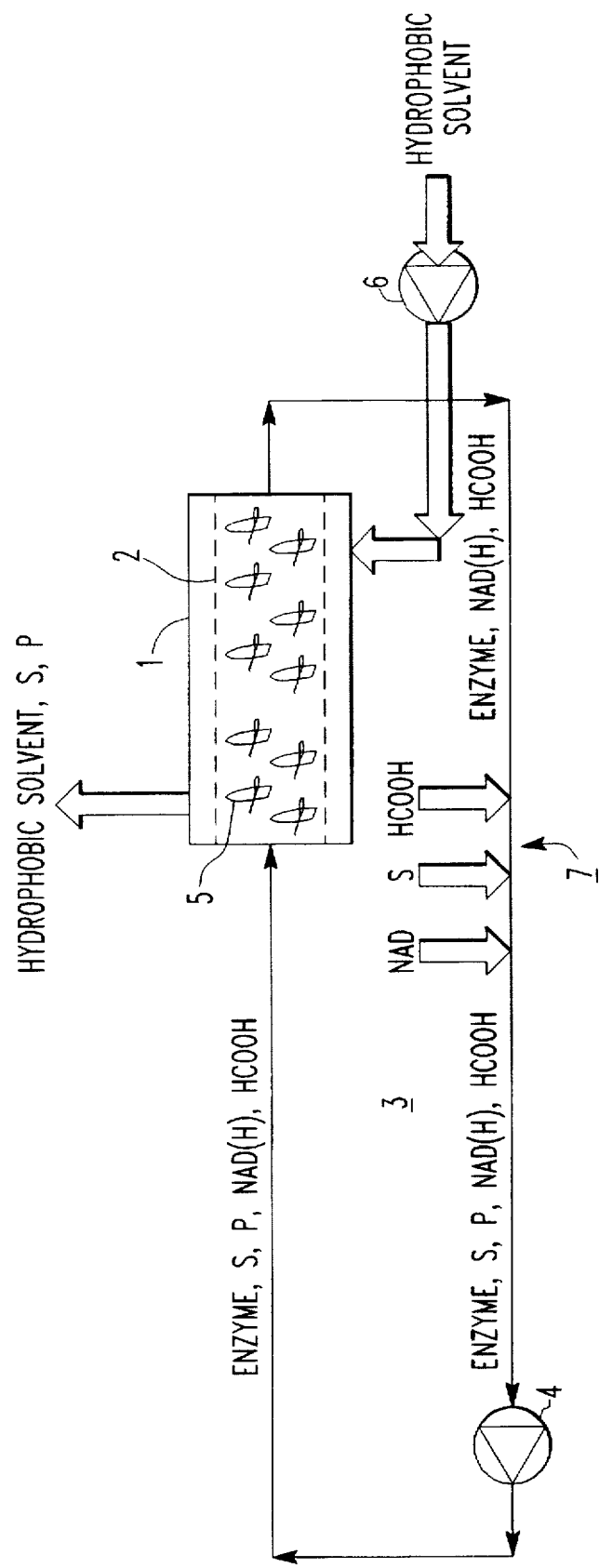
FIG. 3 shows an extraction module in a production facility according to the invention.

The apparatus shown schematically in FIG. 3 includes the extraction module (1) shown in FIG. 1 incorporated into a reactor circuit (3). The reaction solution is circulated in the reactor circuit (3) by a circulating pump (4). In addition to the enzymes (5), the reactor solution contains, upstream of the extraction module (1), the cofactors NAD and NADH, the cosubstrate HCOOH, substrate S which has not been converted, and a product P generated by the enzyme-catalyzed reaction. The latter are extracted within the extraction module (1) into the hydrophobic solvent which is pumped by the extraction solvent pump (6) into the extraction module in counter-current relation to the aqueous phase. By a follow-up dosing step at 7, substrate S is again added to the aqueous flow which, when leaving the extraction module, still contains some hydrophilic components (enzyme, NAD(H), HCOOH). Also, co-substrate HCOOH consumed by reaction and cofactor NAD lost by deactivation are replaced in the follow-up dosing step at 7.

Figure 4:
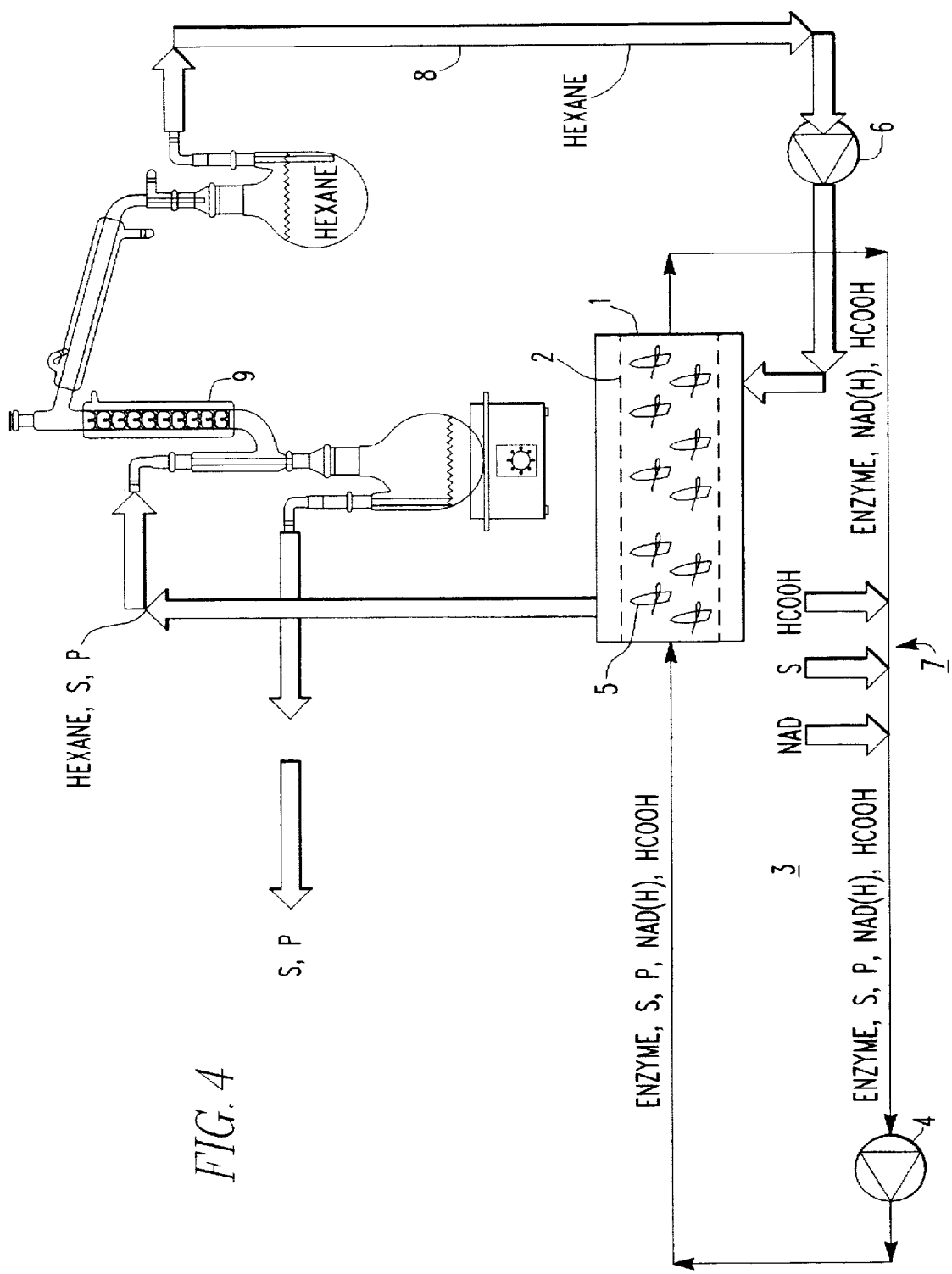
FIG. 4 shows an arrangement according to FIG. 3 coupled with continuous extraction medium rectification.

The arrangement shown in FIG. 4 corresponds to some extent to that of FIG. 3 with the extraction module (1) and the reactor circuit (3); but it additionally includes a hexane circuit (8). The hexane circuit (8) includes a continuously operating rectification column (9) in which the extracted substances (substrate S, product P) are separated from the extraction solvent hexane.

The rectified hexane is returned by the extraction solvent pump (6) to the extraction module (1). As a result, the effective amount of solvent required for the extraction is reduced.

Figure 5:
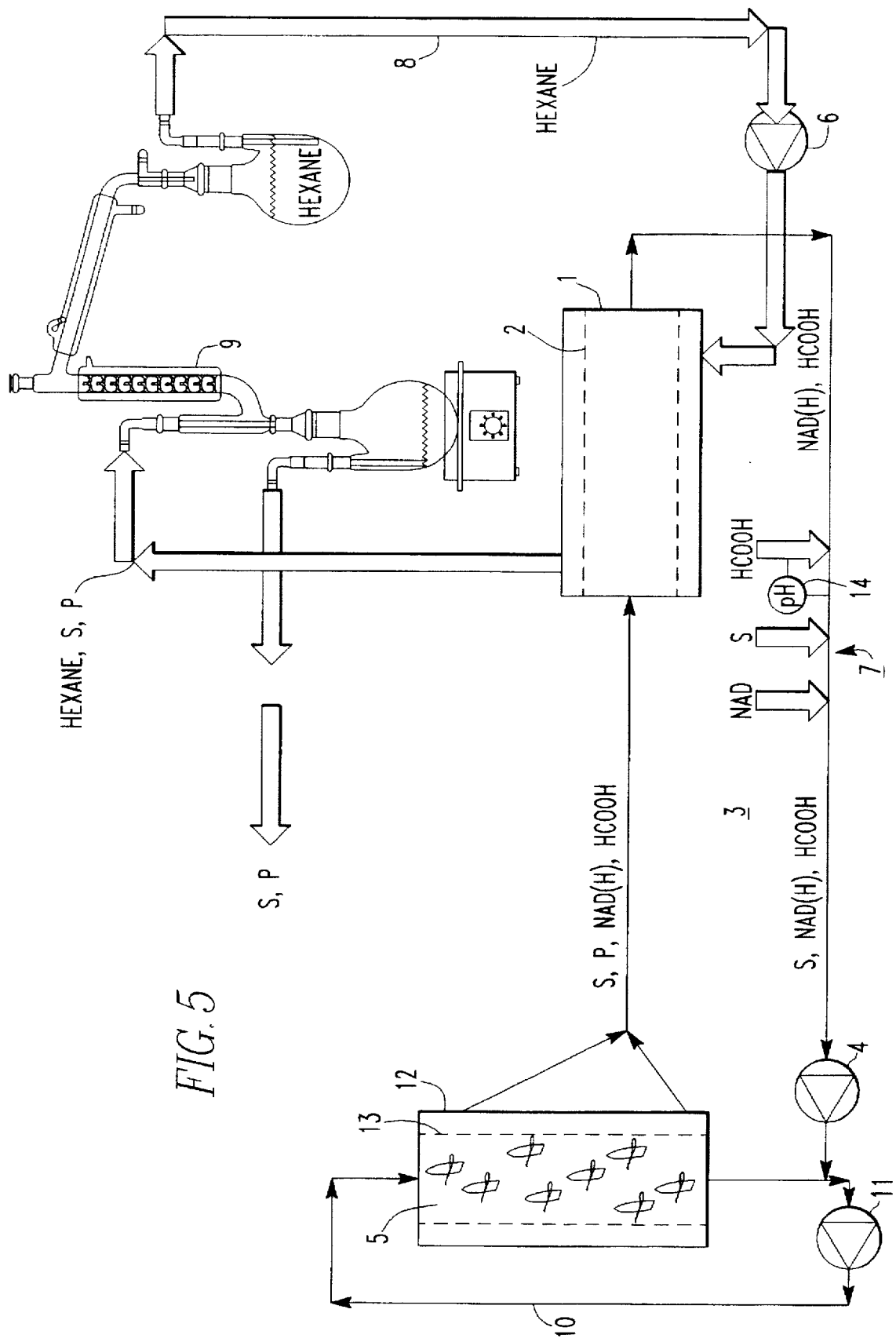
FIG. 5 shows a production plant with an enzyme membrane reactor disposed ahead of the extraction module.

The arrangement according to the invention as shown in FIG. 5 comprises a reactor circuit (3), in which a substrate solution comprising substrate S, cofactors NAD(H) and cosubstrate HCOOH are pumped into the enzyme membrane reactor (10) by the reactor circulating pump (4). The enzyme membrane reactor (10) comprises a circuit consisting of the enzyme circulating pump (11) and the ultra-filtration hollow fiber module (12). In this circuit, the enzymes (5) are immobilized behind a hydrophilic ultra-filtration membrane (13).

From the enzyme-free product solution leaving the enzyme membrane reactor (10) at the filtrate side of the ultrafiltration hollow fiber module (12), the non-converted substrate S and the formed product P are extracted into a continuous hexane flow. The hexane flow containing the substrate S and the product P is divided, in a continuously operating rectification column (9), into a substrate S/product P mixture and hexane. The hexane is returned to the extraction module (1) by way of the hexane circuit (8).

The aqueous solution which was depleted of the product P by the extraction can, after replenishing with the substrate S and the co-factor NAD at (7) and after pH-controlled replenishing of co-substrate HCOOH at (14), be returned to the enzyme membrane reactor (10).

The arrangement as schematically shown in FIG. 5 was used for the production of (S)-1-phenyl-2-propanol. The process parameters are given in the following example.

EXAMPLE 1

In a 50 ml enzyme membrane reactor (EMR) with an ultra-filtration hollow fiber module (amicon hollow fiber, type H1P10-43, cut off :10000Da) with associated circulating pump, there were provided in an aqueous solution the enzymes:

Alcohol dehydrogenase from *Rhodococcus erythropolis*

0.9 U/ml EMR-Vol.

Formaldehydrogenase from *Candida boidinii*

1.9 U/ml EMR-Vol.

and as reactor mixture, there was supplied an aqueous solution with a pH 6.7 including phenyl acetone 9 mM NAD 0.124 mM sodium formate 50 mM formic acid 14.15 mM dipotassium hydrogen phosphate 60 mM.

With an average residence time in the EMR of 0.33 h (total reactor circulation flow: 150 ml/h) and a reaction temperature of 20° C., the conversion rate with respect to the substrate phenylacetone was 73%.

The product solution leaving the enzyme membrane reactor was continuously supplied to a liquid/liquid hollow fiber extraction module (Liqui-Cel® phase contact laboratory module 5PCM-106 of Hoechst Celanese Corp.) having a hydrophobic microporous polypropylene membrane (membrane surface: 0.23 $m^2$; effective pore size: 0.05 μm). Here, (S)-1-phenyl-2-propanol and the non-converted phenylacetone were continuously extracted from the product solution by a continuous hexane counter current flow (1000 ml/h). The product-containing hexane solution was submitted to a continuous rectification and the rectified hexane was again pumped to the extraction module. The total volume of the hexane phase was 800 ml.

The penetration of the hexane through the hydrophobic membrane was prevented by the application of an excess pressure of 0.5 bar on the aqueous side.

The product-free aqueous solution leaving the extraction module was made re-usable as reaction solution by means of continuous follow-up addition of phenyl acetone (1.35 mmol/h) pH-controlled follow-up addition of formic acid and replacement of the co-factor (0.724 µmol/h) which was lost by deactivation, and was re-supplied to the enzyme membrane reactor.

The total volume of the aqueous phase was 450 ml.

The space/time yield based on the EMR volume was 64.3 g/($L_{EMR}$×d).

The total turnover number of the cofactor was 1361 mol$_p$/mol$_{NAD}$ (73%×1.35×1000/0.724 µmol$_p$/mol$_{NAD}$).

For comparison, the total turnover number of the cofactor, that is, without continuous product extraction from the recycle flow returning to the EMR is 53 mol$_p$/mol$_{NAD}$ ((73%×9.0/0.124 µmol$_p$/mol$_{NAD}$).

Consequently, with the extractive recycling according to the invention, a 25 times better utilization of the expensive cofactor is obtained.

In accordance with the invention, the continuous product removal out of the reaction liquid which otherwise is altogether returned to the enzyme reactor almost eliminates the need for the otherwise necessary continuous feeding of the cofactor into the EMR (generally together with the substrate solution); only the losses which amount to only a few percent of the required total (caused by thermal deactivation) have to be made up. Hydrophobic membranes, particularly in the form of hollow fiber bundles as explained earlier have been known and are available for at least 10 years, but their extraordinarily useful effects for the enzymatic production of hydrophobic products has not been utilized.

EXAMPLE 2

4-Phenyl-2-butanon was reduced to (S)-4-phenyl-2-butanol under the same conditions as in example 1.

By continuous addition of substrate, an admission concentration of 4-phenyl-2-butanol in the EMR circuit of 12 mmol/L was established. In order to achieve a sufficiently high conversion rate, the NAD(H) concentration had to be increased to 1.2 mmol/L.

With a residence time of 0.33 hrs in the EMR, the average conversion rate was 80% at a space-time yield of 103.8 g/(lxd).

Corresponding to the deactivation of the cofactor, the co-factor was replenished at a rate of 9.1 µmol/hr.

The total turnover number of the cofactor was 158 mol$_p$/mol$_{NAD}$. The total turnover number of the cofactor on a comparison basis, that is, without extraction and recycling, is 8 mol$_p$/mol$_{NAD}$. In comparison with example 1, these values for the total turnover number are lower because of the required higher concentration of the cofactor of 1.2 mmol/L.

Still, also here a twenty times better utilization of the cofactor is obtained by the extractive recycling according to the invention.

EXAMPLE 3

Methyl-5-hepten-2-on was reduced to (S)-6-methyl-5heptene-2-ol ((S)-(+)-Sulcatol) under the same conditions as in example 1. (S)-(+)sulcatol is the male pheromone of the bark beetle Gnathotrichos sp. and can be used as attraction compound in traps for pest control.

By a continuous substrate addition, the admission concentration of 6-methyl-5-hepten-2-on in the EMR-circuit was adjusted to 10 mmol/L. The stationary NAD(H) concentration was adjusted to 0.2 mmol/L.

With a residence time of 0.33 hrs in the EMR, the average conversion rate was 67% with a space time-yield of 60 g/(lxd).

Corresponding to the deactivation of the cofactor, the cofactor was replenished at a rate of 1.5 µmol/hr.

The total turnover number of the cofactor was 747 mol$_p$/Mol$_{NAD}$. For comparison, that is, without extraction of the product and recycling, the total turnover number is 33 mol$_p$/mol$_{NAD}$.

With the use of the extractive recycling procedure according to the invention, the utilization was improved by the factor 23.

Of course, the method according to the invention is not limited to purely enzymatic processes, but is generally suitable for the separation of hydrophobic products from aqueous reactions mixtures which may inhibit reactions or which may cause follow-up reactions.

What is claimed is:

1. A Process for the continuous enzyme-catalyzed production of hydrophobic products in an aqueous reaction mixture, comprising the steps of: extracting said products from the product-containing reaction mixture, by way of a product-permeable micro-porous membrane, into an organic solvent, and recycling the product-depleted reaction mixture to the production, said process including the step of performing a cofactor-dependent enzymatic reaction and regeneration of said cofactor such that said cofactor remains in said continuous process.

2. A Process according to claim 1, wherein a hydrophobic membrane is utilized.

3. A Process according to claim 1, wherein the enzyme-catalyzed reaction is performed in a reactor having enzymes immobilized therein.

4. A Process according to claim 1, wherein the reaction is performed in an enzyme membrane reactor.

5. A Process according to claim 1, wherein for the separation of the product, the product-containing reaction mixture is conducted through a hollow fiber membrane bundle around which an organic solvent flows.

6. A Process according to claim 5, wherein said organic solvent flows in counter-current fashion to the reaction mixture.

7. A Process according to claim 1, wherein a micro-porous membrane with an effective pore size of 5–500 µm and a differential pressure between aqueous phase and organic solvent of 0.5–5 bar is utilized.

8. A Process according to claim 1, wherein chiral alcohols, amines, cyanhydrine are produced.

9. Process according to claim 1, wherein the organic solvent is recycled in a recycling circuit into which the product extraction is integrated.

10. A process according to claim 9, wherein said product is isolated in said recycling circuit and the substrate is recycled in the process.

11. An Apparatus for the continuous enzyme-catalyzed production of hydrophobic products in an aqueous product solution by way of extraction from a product-containing reaction mixture, according to the method of claim 1, said apparatus comprising a production circuit including an extraction cartridge with a product-permeable microporous membrane exposed, on one (hand) side to said product solution and, on the other, to an organic solvent for the extraction of said product from said aqueous product solution into said organic solvent.

12. An Apparatus according to claim 11, wherein the extraction cartridge comprises a hollow fiber membrane bundle.

13. An Apparatus according to claim 12, further including means for generating a differential pressure between the aqueous and the organic phases in the cartridge.

14. An Apparatus according to claim 11, further including an EMR arrangement for the enzymatic conversion in the production circuit.

\* \* \* \* \*